US00PP32919P2

(12) United States Plant Patent
Danziger

(10) Patent No.: US PP32,919 P2
(45) Date of Patent: Mar. 23, 2021

(54) ***SALVIA* PLANT NAMED 'DSALAXBL'**

(50) Latin Name: *Salvia nemerosa*
Varietal Denomination: DSALAXBL

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 16/873,031

(22) Filed: Jan. 16, 2020

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Salvia* plant named 'DSALAXBL' is disclosed, characterized by early flowering on compact, upright plants. Plants flower abundantly, producing violet-blue flowers with uniquely colored sepals of purple and green. The new variety is a *Salvia*, normally produced as an outdoor garden or container plant.

2 Drawing Sheets

Figure 1:
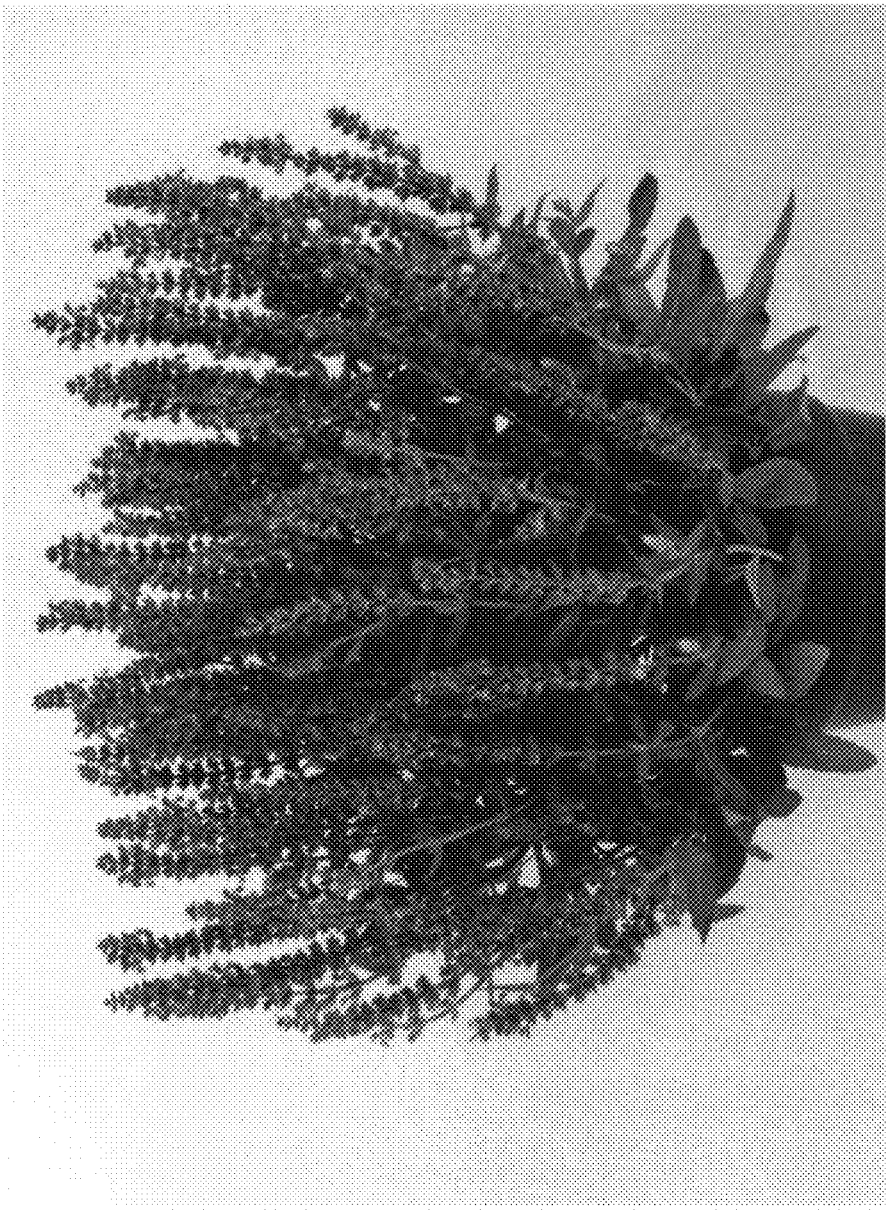

Latin name of the genus and species: *Salvia nemerosa.*
Variety denomination: 'DSALAXBL'.

BACKGROUND OF THE INVENTION

The new *Salvia* cultivar is the product of a planned breeding program conducted by the inventor, Gavriel Danziger, in Moshav Mishmar Hashiva, Israel. The objective of the breeding program was to produce new *Salvia* varieties for ornamental commercial applications. The open pollination resulting in this new variety was made in August 2016.

The seed parent is an, unpatented, unnamed proprietary *Salvia nemerosa* 'SAN-13-2959'. The pollen parent is unknown as it was an open pollination breeding program. The new variety was discovered in June 2017 by the inventor in a group of seedlings resulting from the 2016 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in September 2017, and has shown that the unique features of this cultivar are stable and reproduced true to type in multiple successive generations.

SUMMARY OF THE INVENTION

The cultivar 'DSALAXBL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALAXBL' These characteristics in combination distinguish 'DSALAXBL' as a new and distinct *Salvia* cultivar:

1. Compact and upright habit.
2. Early flowering.

3. Abundant flowers.
4. Violet-blue flowers.
5. Uniquely purple and green colored sepals.

PARENTAL COMPARISON

Plants of the new cultivar 'DSALAXBL' are similar to plants of the seed parent, in most horticultural characteristics, however, plants of the new cultivar 'DSALAXBL' differ in the following;

1. The seed parent has longer foliage than the new variety.
2. The seed parent flowers less abundantly than the new variety.
3. The seed parent has longer flowering stems than the new variety.

COMMERCIAL COMPARISON

Plants of the new cultivar 'DSALAXBL' are comparable to the commercial variety *Salvia* x *sylvestris* 'DSALRS203', U.S. Plant Pat. No. 26,520. The two *Salvia* varieties are similar in most horticultural characteristics; however, the new variety 'DSALAXBL' differs in the following:

1. This comparator blooms one week earlier than the new variety.
2. This comparator has lighter blue petals than the new variety.
3. This comparator has wider foliage than the new variety.

Plants of the new cultivar 'DSALAXBL' can also be comparable to the unpatented commercial variety *Salvia* 'Sallyrosa Pink'. The two *Salvia* varieties are similar in most horticultural characteristics; however, the new variety 'DSALAXBL' differs in the following:

1. This comparator has pink flowers, while the new variety has violet-blue flowers.
2. This comparator has a more erratic growth habit than the new variety.

3. This comparator has green sepals, while the new variety has purple and green sepals.

BRIEF DESCRIPTION OF THE PHOTOGRAPHS

The accompanying photograph in FIG. 1 illustrates in full color a typical plant of 'DSALAXBL' grown in 25 cm pot outdoors in Moshav Mishmar Hashiva, Israel. Age of the plant photographed is approximately 4 months from a rooted cutting.

Figure 2:
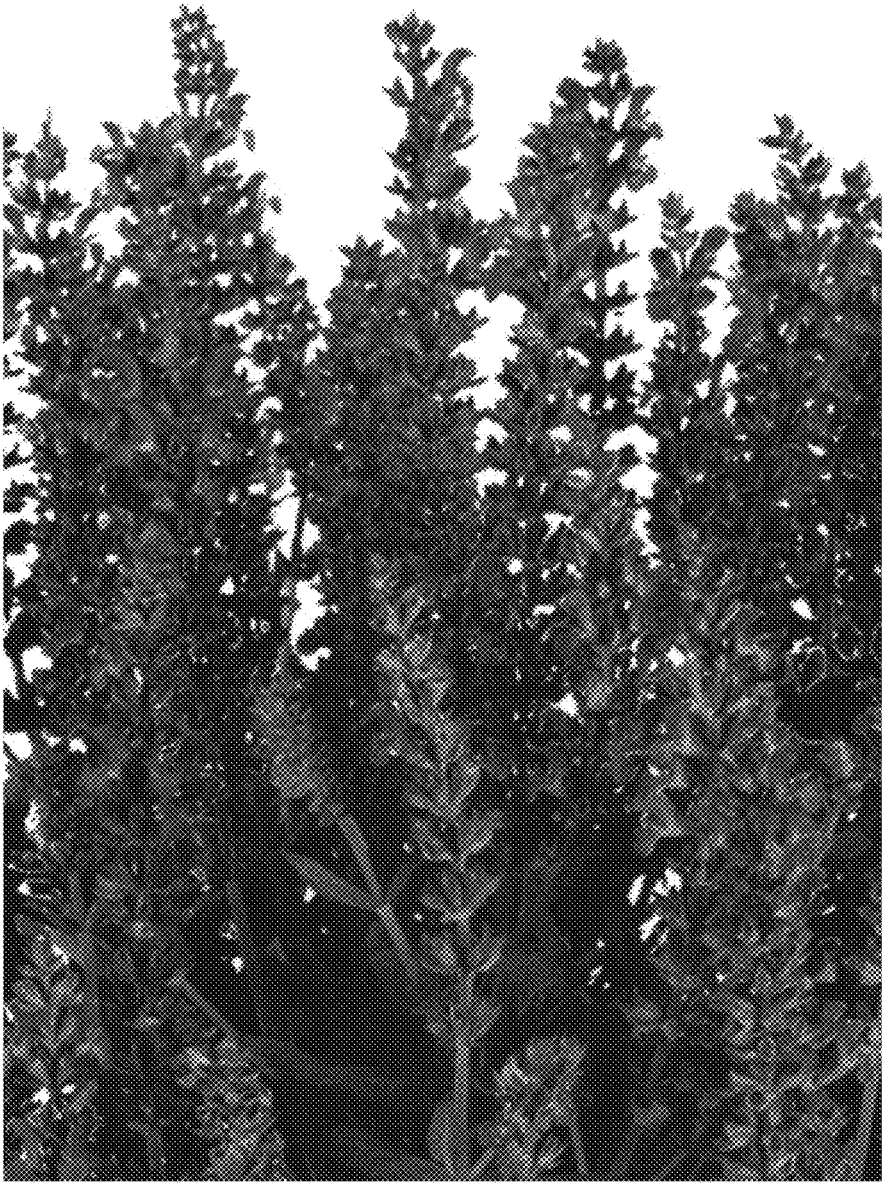

FIG. 2 illustrates multiple inflorescences from the same plant as FIG. 1.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DSALAXBL' plants grown in the Autumn, to Spring in moderate climate in a greenhouse, in Moshav Mishmar Hashiva, Israel. during the night. General light conditions are bright, normal sunlight. Measurements and numerical values represent averages of typical plant types. Botanical classification: *Salvia nemerosa* 'DSALAXBL'.

PROPAGATION

Type of propagation typically used: Vegetative cuttings.
Time to initiate roots: 5-7 days at approximately 18-24° C.
Time to produce a rooted cutting: About 10-14 days at 18-24° C.
Root description: Moderately dense and fibrous. Medium brown in color, not accurately measured with R.H.S. chart.

PLANT

Overall plant shape or growth habit: Compact, spreading and upright.
Plant spread: Approximately 30-35 cm.
Plant height: Approximately 25-30 cm.
Growth rate: Moderate to fast.
Length of primary lateral branches: Approximately 12 cm.
Diameter of lateral branches: Approximately 0.4 cm.
Quantity of lateral branches: About 15.
*Color*.—Near RHS Yellow-Green 144B.
*Texture/pubescence*.—Silky and smooth, velvet like short hairs, stems are slightly ribbed lengthwise.
Internode length: Approximately 5 cm.
Age of plant described: Approximately 12 weeks from a rooted cutting.

FOLIAGE

Leaf:
*Arrangement*.—Opposite.
*Quantity*.—Approximately 6-8 per main branch.
*Average length*.—Approximately 4 cm.
*Average width*.—Approximately 1.5 cm.
*Shape of blade*.—Triangular.
*Apex*.—Rounded.
*Base*.—Some are uneven, some are heart-shaped.
*Attachment*.—Normal.
*Margin*.—Scalloped.
*Texture of top surface*.—Slightly coarse due to immersed venation.
*Texture of bottom surface*.—Slightly coarse due to immersed venation.
*Color*.—Young foliage upper side: Near RHS Yellow-Green 146B. Young foliage under side: Near RHS Yellow-Green 144A. Mature foliage upper side: Near RHS Green N137A. Mature foliage under side: Near RHS Green 137B.
*Venation*.—Type: Pinnate. Venation color upper side: Near RHS Yellow-Green 147D. Venation color under side: Near RHS Yellow-Green 147C.
*Petiole*.—Average Length: Approximately 1 cm. Diameter: Approximately 0.2 cm. Color: Near RHS Yellow-Green 145C.

FLOWER

Natural flowering season: Under moderate climate such as in Israel—from end of Winter to late Fall (February-November). Under cooler weather condition will flower from April to September.
Inflorescence type and habit: Verticillasters, oblong, narrow, and upright habit.
Flower longevity on plant: About 5 days.
Quantity of flowers: About 30 blooming spikes per plant.
Inflorescence size:
*Diameter*.—Approximately 2 cm.
*Height*.—Approximately 15 cm.
*Flowers and buds per inflorescence*.—Approximately 30-34.
Peduncle:
*Length*.—3.5 cm.
*Diameter*.—0.2 cm.
*Texture*.—Silky and smooth, velvet like short hairs, stems are slightly ribbed lengthwise.
*Color*.—Near RHS Yellow-Green 146B.
*Orientation*.—Upright.
*Strength*.—Strong and flexible.
*Petal arrangement*.—The corolla is sympetalous and typically bilabiate with 2 small, highly fused lobes forming an upper lip and 3 (2 small on the sides, one large in the middle) larger highly fused lobes forming a lower lip.
Individual flowers:
*Diameter*.—Approximately 0.5 cm.
*Length*.—Approximately 1 cm.
*Persistence*.—Non-persistent.
*Fragrance*.—None.
Petals:
*Margin*.—Entire.
*Tip shape*.—Upper lip: Rounded. Lower lip: Blunt.
*Length*.—Upper lip: 0.5 cm. Lower lip: 0.2 cm. Tube: 0.3 cm.
*Width*.—Upper lip: 0.2 cm. Lower lip: 0.6 cm. Tube: 0.1-0.2 cm.
*Texture*.—Upper lip: Smooth, slightly pubescent, matte. Lower lip: Smooth. Tube: Smooth, transparent, slightly ribbed lengthwise.
*Color*.—Upper Lip, when opening: Near RHS Violet-Blue N89D. Upper Lip, fully opened: Inner surface: Near RHS Violet-Blue N89D. Outer surface: Near RHS Violet-Blue N89C. Lower Lip, fully opened: Inner surface: Near RHS Violet N88A. Outer surface: Near RHS Violet 90A. Tube, fully opened: Inner surface: Near RHS White N155C. Outer surface: Near RHS White N155C.

Bud:

*Shape*.—Claviform.
*Length*.—0.6 cm.
*Diameter*.—0.2 cm.
*Color*.—Near RHS Violet N88A.

Sepals:

*Shape*.—2 lobes fused at base to form a tube.
*Length*.—Approximately 0.7 cm.
*Width*.—Approximately 0.4 cm.
*Margin*.—Entire.
*Texture*.—Lightly pubescent with soft, short feather-like hairs.
*Color*.—RHS Purple N77A mixed with Green N137A.

REPRODUCTIVE ORGANS

Stamens:

*Number*.—2.
*Filament length*.—Approximately 0.7 cm.

Anthers:

*Shape*.—Oblong.
*Length*.—Approximately 0.15 cm.
*Color*.—RHS Purple 79B.
*Pollen*.—Moderate quantity.
*Pollen color*.—Near RHS Purple 79D.

Pistil:

*Number*.—1.
Length.—Approximately 1.2 cm.
*Style*.—Length: Approximately 1 cm. Color: RHS Purple 76C.
*Stigma*.—Shape: V-shaped. Color: RHS Violet-Blue N89A. Ovary color: Near RHS Yellow-Green 146C.

OTHER CHARACTERISTICS

Seeds and fruits: Up to four seeds per fruit, colored near RHS Brown Group N200A.

Disease/pest resistance: Neither resistance nor susceptibility to normal diseases and pests of *Salvia* has been observed.

Temperature tolerance: USDA Zones 4-9

Drought tolerance: Not tolerant to drought.

What is claimed is:

1. A new and distinct cultivar of *Salvia* plant named 'DSALAXBL' as herein illustrated and described.

* * * * *